United States Patent [19]

Jones et al.

[11] Patent Number: 5,132,018
[45] Date of Patent: Jul. 21, 1992

[54] ISOCONDUCTIVE GRADIENT ION CHROMATOGRAPHY

[75] Inventors: William R. Jones, Blackstone; Allan L. Heckenberg, Hudson; Petr Jandik, Framingham, all of Mass.

[73] Assignee: Millipore Corporation, Bedford, Mass.

[21] Appl. No.: 729,775

[22] Filed: Jul. 10, 1991

Related U.S. Application Data

[63] Continuation of Ser. No. 361,792, May 30, 1989, abandoned, which is a continuation of Ser. No. 196,312, May 20, 1988, abandoned.

[51] Int. Cl.$^5$ ............................................. B01D 15/08
[52] U.S. Cl. ................................. 210/656; 210/198.2
[58] Field of Search ............ 210/635, 656, 659, 198.2; 422/70; 436/150

[56] References Cited

U.S. PATENT DOCUMENTS

| | | | |
|---|---|---|---|
| 4,073,725 | 2/1978 | Takeuchi | 210/659 |
| 4,500,431 | 2/1985 | Miyanaga | 210/198.2 |
| 4,519,996 | 5/1985 | Knochel | 423/580 |
| 4,699,718 | 10/1987 | Jones | 210/198.2 |
| 4,751,189 | 6/1988 | Rocklin | 210/656 |

OTHER PUBLICATIONS

Shintani, "Gradient Anion Chromatography with Hydroxide and Carbonate Eluents Using Simultaneous Conductivity and pH Detection", Anal. Chem., vol. 59, pp. 802-808, No. 6, Mar. 15, 1987.
Dasgupta, "Ion Chromatographic Separation of Ion Interaction Reagents and Annular Helical Suppressor", Anal Chem. vol. 56, No. 4, Apr. 1984, pp. 769-772.
Tarter, "Gradient Ion Chromatographic Determination of Inorganic Anions Using a Continuous Gradient", Anal.-Chem. vol. 56, No. 8, Jul. 1984, pp. 1264-1268.
Sunden, "Separation of Sulfite, Sulfate, and Thiosulfate by Ion Chromatography with Gradient Elution", Anal. Chem. vol. 55, No. 1, Jan. 1983, pp. 2-4.
Berry et al., "Matching Refractive Index of LC Solvents", *American Laboratory*, 18:57-66 (Aug. 1986).
Gjerde et al., "Ion Chromatography, 2nd Edition", A. Huethig Verlag (New York 1987), pp. 93-128.

*Primary Examiner*—Ernest C. Therkorn
*Attorney, Agent, or Firm*—Hamilton, Brook, Smith & Reynolds

[57] ABSTRACT

An improved gradient ion chromatography process is disclosed. The process employs a gradient eluent which is maintained in a substantially isoconductive state throughout each sample run. By maintaining the gradient in an isoconductive state, conductivity detection and analysis of eluted analytes is enhanced.

10 Claims, 4 Drawing Sheets

ISOCONDUCTIVE GRADIENT ION CHROMATOGRAPHY

This is a continuation of application Ser. No. 07/361,792 filed on May 30, 1989, which is a continuation of Ser. No. 196,312 filed May 20, 1988, both now abandoned.

BACKGROUND OF THE INVENTION

Recent advances in ion chromatography have involved a technique referred to as gradient elution. This technique, in which the composition of the mobile phase eluent is varied over time, has been found to be very useful when analyzing samples containing a mixture of both weakly retained anions and strongly retained anions The most common method of gradient elution uses a two solvent gradient in which elution is begun using a weak solvent. This is followed by a continuous or stepwise increase of concentration of a second, stronger solvent until the solution consists entirely of the stronger solvent.

Unfortunately, gradient elution has been considered difficult or impossible to accomplish with liquid chromatography systems which utilize bulk property detectors such as those measuring conductivity or refractive index of chromatography column eluates. This is because the changes in composition of the mobile phases required during gradient evolution generally resulted in a change which was too large to be handled by the bulk property detectors. The relatively small deflections resulting from zones of analytes passing through the detector cell after their separation by gradient elution often were thought to remain undetected at the crude sensitivity setting imposed by the simultaneously occurring change in the bulk concentration of the eluent.

Recently, however, there have been reports of successful sample analysis via conductivity using the gradient elution method. See for example, Sunden, et al., *Anal. Chem.*, 55, 2–4 (1983); Dasgupta, *Anal. Chem.*, 56, 769–772 (1984); Tarter, *Anal. Chem.*, 56, 1264–1268 (1984); and Shintani, et al., *Anal. Chem.*, 59, 802–808 (1987). Additionally, attempts have been made using refractive index detection subsequent to gradient elution as reported by Berry, et al. in *American Laboratory*, 18, 57–66 (1986).

In each of the above references, the conductivity detection methods have been made compatible with gradient elution by employing external chemical devices, called suppressors, between the chromatographic separation column and the detector. While suppressors generally function to convert high conductivity signals to low level background readings, they can also be used to reduce the large change in conductivity which results from the conventional gradient elution techniques. Software methods are then required to subtract the baseline of blank gradients to improve the appearance of the obtained recordings. Additionally, the software methods enable an evaluation of peak heights and areas. In the absence of chemical suppressors, the computer aided baseline subtraction is insufficient to enable a reproducible evaluation of peak heights and peak areas when using conductivity detection in conjunction with conventional gradient elution techniques.

SUMMARY OF THE INVENTION

This invention pertains to a gradient ion chromatography process which eliminates the need for chemical suppressors and complex baseline subtraction regimens. More specifically, the invention pertains to a gradient ion chromatography process wherein the mobile phase solvent remains in a substantially isoconductive state despite its change in composition throughout the gradient program. The mobile phase, or eluent, can have a variable cationic composition ranging from a high ionic equivalent conductance to a low ionic equivalent conductance. However, by a proper selection of counter cations present in the mobile phase, a substantially isoconductive state can be maintained throughout a compositional changeover between two eluents of different eluting strength.

The use of an isoconductive mobile phase eliminates the need for chemical suppressors and suppressor regenerants which have traditionally been required for gradient ion chromatography. However, the advantages of a process employing gradient elution are retained. These include the ability to determine large numbers of ions in a single run and the ability to determine trace ions in the presence of excess concentrations of other ionic compounds. Additionally, the isoconductive gradient process provides the ability to separate mixtures of weakly and strongly retained ions while maintaining a uniform and efficient level of separation efficiency throughout the entire separation.

DETAILED DESCRIPTION OF THE INVENTION

The most common type of gradient eluent employed in gradient ion chromatography employs a two solvent gradient. Generally, elution begins with a weak solvent to which increasing concentrations of a stronger solvent are added continuously or in a step-wise manner until the eluent comprises a solution containing entirely strong solvent. This method of gradient elution is considered the easiest to conduct. The variation of solvent composition over time, referred to as the solvent program, is the most important variable in gradient ion chromatography.

For two given solvents, A and B, a continuous program can be described by the shape and by the steepness or rate of change of the composition curve of the component mixture. Each of these features can greatly affect the quality of the separation. Additionally, the choice of the solvents themselves is important in the design of adequate gradient elution separation processes.

In choosing the particular solvents used, the general requirement is that the first solvent, A, be weak enough to give adequate resolution at the front end of the chromatogram, and that the second solvent, B, be strong enough to provide elution of the strongly retained analytes within a reasonable total separation time.

Figure 1A:
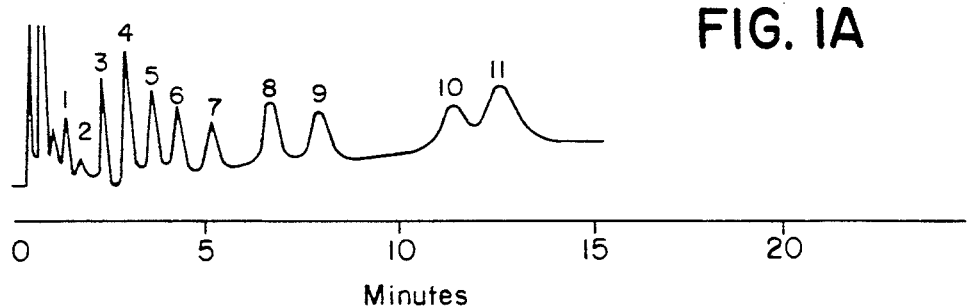
FIG. 1A is a chromatogram resulting from an isoconductive eluent comprising a gradient of the solvents of FIGS. 1B and 1C.

FIG. 1A shows a chromatogram which results from a proper selection of solvents A and B. In FIG. 1A, all sample components have been eluted at optimum concentrations of A and B as adequately resolved bands.

Figure 1B:
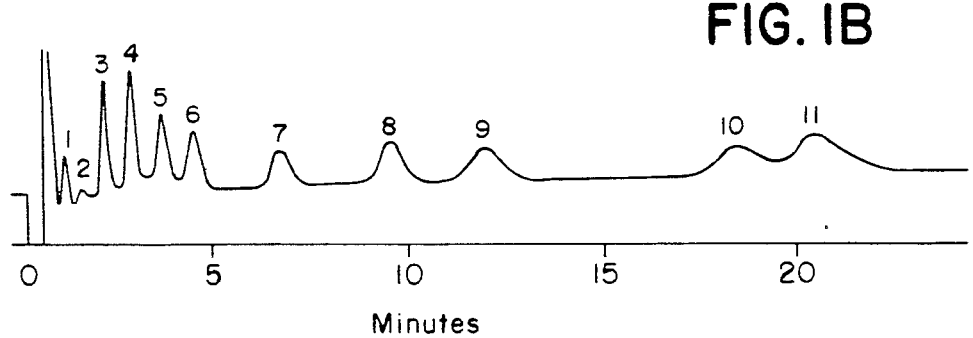
FIG. 1B is a chromatogram resulting from an isocratic eluent comprising a weak eluting solvent.
Figure 1C:
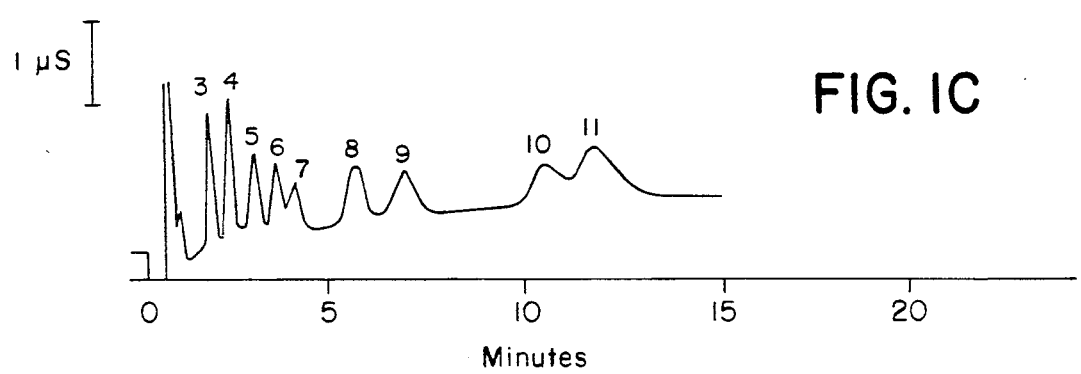
FIG. 1C is a chromatogram resulting from an isocratic eluent comprising a strong eluting solvent.

FIGS. 1B and 1C are representative chromatograms which result when the eluents are less then ideal for the specific sample. In FIG. 1C, starting solvent A is too strong. As a result of this, several bands are clustered at the front end of the chromatogram and are poorly resolved. FIG. 1B represents a chromatogram resulting when the eluent is too weak. Later eluted bands show peak broadening and unacceptably long separation time. The final bands to elute would probably be undetectable at any slightly lower concentration of analyte or eluent.

In conventional gradient ion chromatography, the conductivity baseline, which results from the eluent phase rather than from the analytes, varies with the changes in eluent composition. This variation of the baseline leads to complex schemes to minimize the inaccuracies it introduces into the system. These include the use of chemical suppressors to minimize the baseline signal and software to convert the variable baseline to a signal which is as flat as possible.

Figure 2:
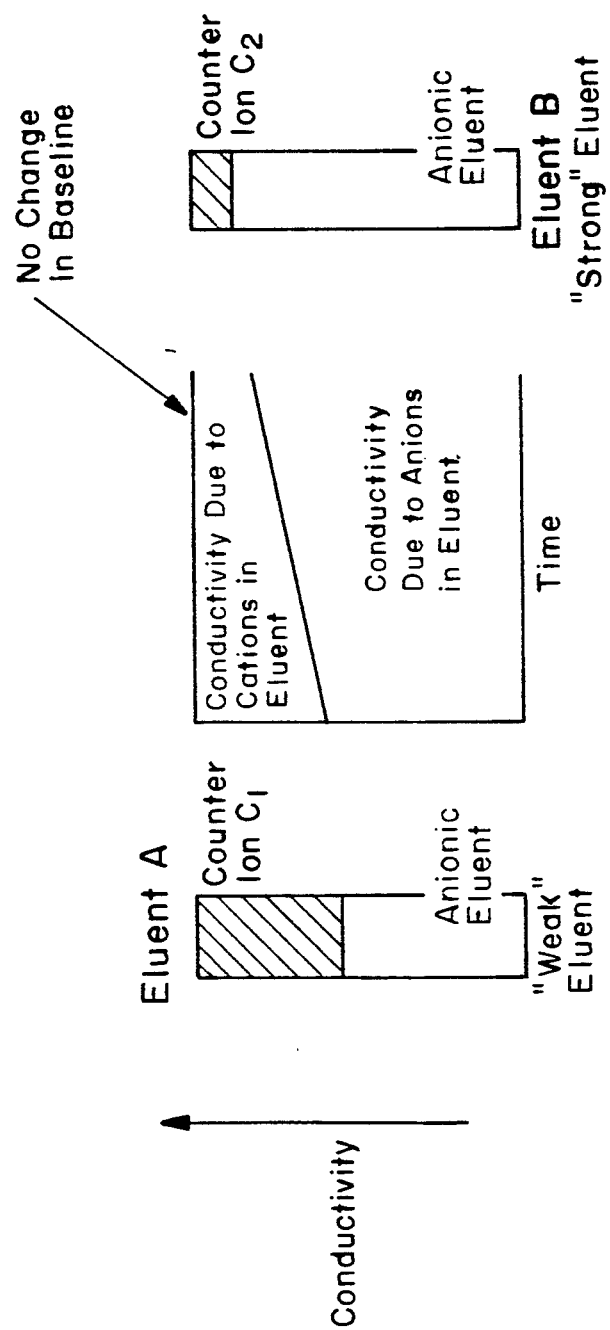
FIG. 2 is a representation of the content and conductivity of eluents used with a solvent program compatible with this invention.

By selecting solvents A and B which maintain an isoconductive state throughout the gradual or step-wise composition gradient, the need for chemical suppressors and sophisticated baseline manipulation is eliminated. This approach is illustrated in FIG. 2. In FIG. 2, the solvents are chosen such that the weaker eluent contains cations with high ionic equivalent conductance and the stronger eluent contains cations with low ionic equivalent conductance. Thus, over the course of the solvent mixing program, the anionic eluting strength of the eluent can increase without changing the background conductance significantly. This produces an essentially flat baseline which can be evaluated for quantitative results by relatively uncomplicated software methods.

A formula for calculating the background conductance signal, G, resulting from a fully dissociated ionic mobile phase was described by Gjerde et al. in "Ion Chromatography", 2nd edition, A. Huethig Verlag (New York 1987), pp. 93–128. This formula is represented as Equation (1):

$$G = \frac{(\lambda_c + \lambda_a)}{K(10^{-3})} c \qquad (1)$$

wherein $\lambda_c$ and $\lambda_a$ are cationic and anionic equivalent conductances in $cm^2 equiv^{-1} ohm^{-1}$. The concentrations in $equiv\ liter^{-1}$ and cell constant in $cm^{-1}$ are represented as c and K respectively.

For any two isoconductive mobile phases with a common anion $A^{n-}$ and two different cations, $c_1$, and $c_2$, it is possible to derive an expression which links the ratio of the weaker ($C_1$) and stronger ($C_2$) concentrations with the corresponding equivalent conductances. This expression is given in Equation (2):

$$\frac{C_2}{C_1} = \frac{\lambda c_1 + \lambda_a}{\lambda c_2 + \lambda_a} \qquad (2)$$

Equation 2 facilitates the search for optimum ionic concentrations in isoconductive eluents. As determined by this relationship, large concentration ratios are possible only with eluents containing anions having low ionic equivalent conductance. For example, with hydroxide, ($\lambda_{OH}=198$), and borate/ gluconate, ($\lambda_{BG}=25.5$), the values of $C_2/C_1$ for a potassium to lithium gradient step are 1.1 and 1.5 respectively. Results obtained using equation (2) are found to be in good agreement with data determined experimentally. A practical value for an isoconductive increase of the gluconic acid concentration in the presence of an appropriate concentration of boric acid, using potassium and lithium hydroxides for conductivity adjustments was determined to be 1.5, a value that is equal to the value calculated using equation (2).

The background conductance of a variety of eluents is given in Table I.

TABLE I

| Counter-ions | Borate Gluconate pH 8.5, 1 mM | Benzoic Acid pH 4.8, 2 mM | Phthalic Acid pH 5.6, 1 mM | Trimesic Acid pH 4.0, 0.5 mM |
|---|---|---|---|---|
| Na+ | 260 | 175 | — | — |
| Li+ | 215 | 132 | 154 | 93 |
| TBA+ | 220 | 130 (pH 4.9) | — | — |

The limiting equivalent ionic conductances in aqueous solutions at 25° C. are given for a variety of anion and cations in Table II.

TABLE II

| Anions | $\lambda_a$ | Cations | $\lambda_c$ |
|---|---|---|---|
| Benzoate | 32.4 | H+ | 349.7 |
| O-Phthalate | 52.3 | Li+ | 38.7 |
| F− | 55.4 | Na+ | 50.1 |
| Cl− | 76.3 | K+ | 73.5 |
| $NO_2^-$ | 71.8 | TBA+ | 19.5 |
| Br− | 78.1 | | |
| $SO_4^{-2}$ | 80 | | |
| $NO_3^-$ | 71.4 | | |

A variety of external factors can considerably affect the overall performance of the isoconductive gradient elution method. For example, it is necessary to suppress temperature fluctuations. Without appropriate temperature control, conductivity baseline fluctuations can reach orders of magnitude similar to those of conductivity background changes resulting from the gradual compositional shifts of the gradient eluent. Unlike the baseline fluctuations brought about by compositional changes, temperature induced fluctuations tend to be irreproducible.

An efficient temperature control which eliminates most of the irreproducible thermal influence can be achieved by maintaining the eluent reservoirs, the connecting capillaries, the separation apparatus and the conductivity cell at exactly the same temperature. One method for accomplishing this is to place all exposed parts into an insulated box maintained at a slightly elevated temperature, typically about 35° C. Preferably, this method should employ a temperature control means having accuracy of better than ±0.1° C.

For sufficient sensitivity, it is necessary to minimize the crossover contributions of the pump to the baseline noise. This can be accomplished using pumps equipped with specialized software for minimizing noise arising from pump pulsation. Such pumps are available from Waters, Division of Millipore, Bedford, Mass.

Furthermore, it has been found that conductivity changes during the isoconductive gradient method can be further minimized by the employment of shorter columns having extremely low ion exchange capacities. Additionally, column materials having polyacrylate backbone supporting the ion exchange groups have been found to be more suitable than those having styrene-divinyl benzene backbone structures.

The invention will now be more particularly pointed out and in the following, non-limiting examples.

EXPERIMENTAL SECTION

Materials and Apparatus

All chemicals were utilized as obtained from commercial sources, Milli-Q water (Trademark of Millipore Corporation) was used for all aqueous solutions described herein. Each of the standard solutions of inorganic and organic anions used in this study were prepared from sodium or potassium salts of reagent grade purity.

Among the materials used herein, lithium hydroxide monohydrate (99%), potassium hydroxide (86.2%), cesium hydroxide monohydrate (99%), boric acid (99% A.C.S. reagent), and D-gluconic acid (50% wt in $H_2O$) were supplied by Aldrich Chemical Company, Inc. Glycerin (U.S.P.-F.C.C.) and acetonitrile (HPLC grade) were obtained from J. T. Baker Chemical Company.

As equality of conductances is an overriding concern in the preparation of isoconductive eluents, fine adjustments to the eluents were made by small variations of the total added amounts of hydroxide. Since the purity of the hydroxides fluctuated due to changes occurring during storage, small variations in the molar ratios of alkaline hydroxide to other, more stable, components of isoconductance eluents were expected.

All components of the chromatographic system were supplied by Waters Chromatography Division of Millipore Corporation. A programmable M590 high pressure pump was used to control a Solvent Switching Valve connected between the pump on one side and solvent reservoirs containing eluents of different eluting strength on the other side.

An Automatic High Pressure Switching Valve was used as an injector. This was achieved by connecting either a 100 ul or 20 ul sample loop and an injection port to the valve. A signal connection was made between the injector and the M590 pump. Solvent changes resulting in step gradients and also data acquisition by an M840 Chromatographic Data Station were triggered by manual actuation of the injector. As a result of a delay volume of 3 ml and a flow rate of 1.2 ml/min, the changed composition of the eluent reached the separation column about 2.5 minutes after injection for each chromatogram produced. The same delay volume made it possible to change back to eluent B before the current gradient run was completed. Thus, this step could occur almost 2.5 minutes before the elution of the final peak.

Two different columns were used for the gradient experiments. The first was an IC Pak Anion column which had dimensions of 0.46×5.0 cm. This column was packed with a polyacrylate-based anion exchange material. The particle size was 10 microns and an ion exchange capacity of 30 ueq/ml was specified. The second column was an IC Pak Anion HR column having dimensions of 0.46×7.5 cm. The column was packed with 7 micron particles of the polyacrylate resin used in the first column. The ion exchange capacity of the resin of the second column was the same as that of the material used in the first column.

An M430 Detector was employed to measure conductivity changes in the column eluate. The detector cell had a nominal cell constant of one and was maintained at a constant temperature of 35° C. An Extech Model 590 Conductivity Meter was chosen for evaluating the conductivity of solutions which contained solutions of borate and gluconate. The value of the cell constant, (1.0 $cm^{-1}$), was verified by measuring the conductance of a 0.01 N KCl solution. The equivalent conductance of borate gluconate complex was calculated using the conductivity reading obtained from a solution which contained 2.6 mM sodium gluconate (Eastman Kodak P8626), 1.3 mM boric acid and 1.3 mM sodium hydroxide. The value of equivalent conductance of the borate gluconate complex was determined to be 25.5 $cm^2 equiv^{-1} ohm^{-1}$. This value was confirmed by additional measurements in which the borate gluconate ratio was held constant and the concentration of sodium hydroxide was increased in several steps. All measurements were conducted at 25° C.

EXAMPLE I

Comparison of Baseline Conductance

Conductivity changes using an unadjusted gradient eluent and an isoconductive gradient eluent were obtained and compared.

The unadjusted gradient eluent contained solvents designated A1 and B1, each containing potassium as a counterion. Solvent A1 was a solution of 11 mM boric acid, 1.48 mM gluconic acid, 3.49 mM potassium hydroxide, 0.65 mM glycerin and 12% acetonitrile. Solvent B1 was a solution of 13.75 mM boric acid, 1.85 mM gluconic acid, 4.36 mM potassium hydroxide, and 0.81 mM glycerin and 12% acetonitrile.

The isoconductive gradient eluent contained solvents designated A2 and B2. The eluents were adjusted to the same level of conductance using potassium for the weaker mobile phase corresponding to solvent A2 and lithium for the stronger mobile phase corresponding to solvent B2. Solvent A2 was identical to solvent A1 above. Solvent B2 was a solution containing 5.13 mM lithium hydroxide monohydrate, 13.75 mM boric acid, 1.85 mM gluconic acid, 0.81 mM glycerin and 12% acetonitrile. The increased glycerin concentration did not contribute to eluting strength. Rather, the increase was derived from the fact that 25 ml of a fifty-fold concentrate of solvent A1 (without acetonitrile) was used to prepare solvent B2.

Figure 3:
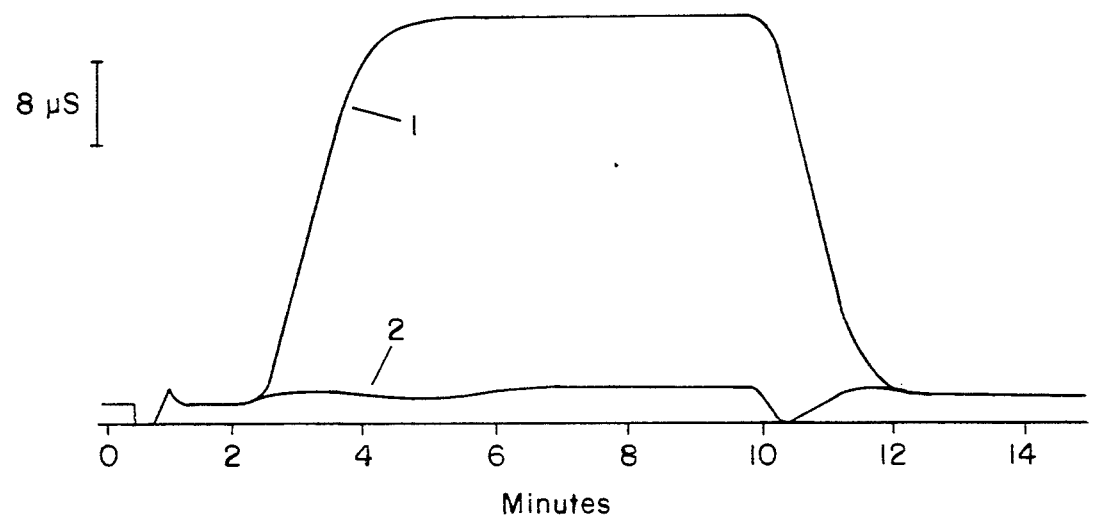
FIG. 3 is a blank chromatogram comparing the conductivity baseline resulting from conventional gradient ion chromatography to the baseline resulting from isoconductive gradient ion chromatography.

The results of the comparison of Example 1 are given in FIG. 3. The unadjusted gradient is designated baseline 1 while the isoconductive gradient is designated baseline 2. As is readily apparent from FIG. 3, the originally overwhelming change of the background signal is efficiently removed via the isoconductive gradient eluent.

The size and shape of the two small baseline disturbances in baseline 2 are largely column independent.

They have been found to remain unchanged even if an anion exchange column is not present in the system. The first fluctuation occurs between 2.5 and 4 minutes as the changing composition of the eluent begins to reach the detector cell. The larger of the two baseline deflections, having an amplitude of about 4 uS is observed at the point that the system is returned to the initial eluent, i.e., between 9.5 and 11 minutes in FIG. 3.

EXAMPLE II

Ion Detection Using Isocratic Elution and Isoconductive Gradients

A sample containing 11 anions was separated using a weak solvent, (A2 of the previous example); a strong solvent, (B2 of the previous example); and an isoconductive step gradient from solvent A2 to solvent B2 which was initiated simultaneously with the sample injection. The sample contained the following anions which are preceded by their peak identities: 1. fluoride 1 ppm, 2. carbonate 2 ppm, 3. chloride 2 ppm, 4. nitrite 4 ppm, 5. bromide 4 ppm, 6. nitrate 4 ppm, 7. phosphate 6 ppm, 8. sulfate 4 ppm, 9. oxalate 4 ppm, 10. chromate 10 ppm, 11. molybdate 10 ppm. The injected sample had a 100 ul volume. The separation column was the IC-Pak anion column previously described.

The three separations are depicted in FIG. 1. The weak anion exchange mobile phase (solvent A2), used to produce the chromatogram of FIG. 1B resulted in satisfactory separation of only the early eluted peaks. The total run time became excessively long (about 20 minutes) and the resulting peak spreading of the late eluting peaks led to a decreased sensitivity of their detection.

A chromatogram produced using a stronger eluent, (Solvent B2), is presented in FIG. 1C. The stronger eluent led to reduced run times and reduced peak spreading for the strongly retained anions. Unfortunately, however, the stronger eluent caused a deterioration of the separation in the initial portion of the chromatogram. Additionally, the first two peaks, resulting from fluoride and carbonate, were lost in the strong eluent separation.

A chromatogram produced using the isoconductive gradient, in which solvents A2 and B2 are simultaneously employed, is presented in FIG. 1A. The gradient solution combines the advantages of the weak and strong eluents in one separation, thereby providing a short run time and good separation of early eluting analytes. For example, in the chromatogram of FIG. 1A, an efficient separation is achieved in the initial portion, while the total run time is very similar to the shortened run times characteristic of stronger eluents.

The chromatogram of FIG. 1A was obtained by subtracting the blank isoconductive gradient (baseline 2 of FIG. 3), from the actual raw chromatographic recording. The reproducibility of these subtractions, (and of the whole isoconductive gradient), was tested via six repetitions of the gradient separation of FIG. 1A. Relative standard deviations (RSDs) of the retention times and of the integrated areas for each of the eleven separated peaks are given in Table III.

TABLE III

| Anion | Peak Areas % RSD 6 Runs | Retention Time % RSD 6 Runs |
| --- | --- | --- |
| fluoride | 3.7 | 0.7 |
| chloride | 0.9 | 0.3 |
| nitrite | 1.6 | 0.2 |

TABLE III-continued

| Anion | Peak Areas % RSD 6 Runs | Retention Time % RSD 6 Runs |
| --- | --- | --- |
| bromide | 3.5 | 0.2 |
| nitrate | 2.4 | 0.2 |
| phosphate | 3.4 | 0.2 |
| sulfate | 2.0 | 0.3 |
| oxalate | 1.7 | 0.2 |
| chromate | 0.5 | 0.4 |
| molybdate | 1.1 | 0.4 |

As can be seen in Table III, the gradient elution with the borate gluconate anion and the selected counter cations is highly reproducible, achieving better than a ±0.5% precision of retention times for the majority of analyzed anions. The observed values of %RSD for peak areas, (0.8–3.8% for the concentration range 1–6 ppm and 0.5–1.7% for 10 ppm), make the isoconductive gradient elution acceptable for a variety of common applications.

EXAMPLE III

High Resolution Ion Detection Using an Isoconductive Gradient

A sample containing 14 anions was separated using a high resolution column (IC-Pak Anion HR) previously described. The weak solvent, designated A3, was a solution of 8.25 mM boric acid, 1.11 mM gluconic acid, 3.08 mM cesium hydroxide, 0.48 mM glycerin and 12% acetonitrile. The stronger solvent, designated B3, was a solution of 12.65 mM boric acid, 1.70 mM gluconic acid, 4.72 mM lithium hydroxide, 0.75 mM glycerin and 12% acetonitrile.

A isoconductive step gradient from A3 to B3 was initiated at the moment of injection. At the eighth minute, the flow rate of the mobile phase was increased from 1.2 ml/min to 1.7 ml/min. The injected sample had a volume of 20 ul.

Figure 4:
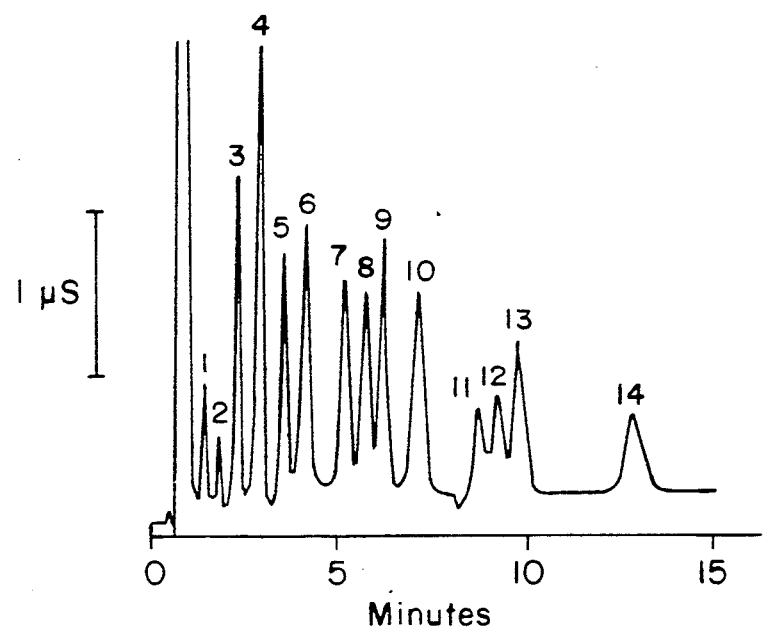
FIG. 4 is a high resolution chromatogram produced using an isoconductive gradient elution of a fourteen-anion sample mixture.

The resulting chromatograph is presented as FIG. 4. In FIG. 4, a short run time along with good resolution of the early eluted species is observed. The sample of FIG. 4 contained the following anions which are preceded by their peak identities: 1. fluoride, 5 ppm; 2. carbonate, 20 ppm; 3. chloride, 15 ppm; 4. nitrite, 20 ppm; 5. bromide, 20 ppm; 6. nitrate, 20 ppm; 7. phosphate, 30 ppm; 8. phosphite, 20 ppm; 9. sulfate, 20 ppm; 10. oxalate, 20 ppm; 11. tungstate, 25 ppm; 12. chromate, 25 ppm; 13. molybdate, 25 ppm; and 14. thiocyanate, 25 ppm.

EQUIVALENTS

Those skilled in the art will recognize, or be able to ascertain applying no more than routine experimentation, many equivalents to the specific embodiments described herein. Such equivalents are intended to be encompassed within the following claims.

We claim:

1. A gradient ion chromatography process for determining the ionic content of a sample comprising the steps of:

providing a first eluent comprising a first anionic and cationic composition;

flowing the first eluent through an ion chromatography column;

injecting the sample to be analyzed into the first eluent stream in a manner which allows the sample to flow through the ion exchange column;

increasing eluting strength by replacing the first eluent with a second eluent comprising a second cationic and anionic composition of same conductivity as the first eluent but having an increased eluting strength thereby increasing eluting strength while maintaining said eluent in a substantially electrically isoconductive state, to eliminate the need for chemical suppressors and to avoid the need for complex baseline subtraction regimens; and continuously measuring the electrical conductivity of the eluate stream exiting the ion chromatography column, wherein a chemical suppressor stage external to the ion chromatography separation column is not necessary.

2. A process as in claim 1 wherein the composition of the eluent is varied from a composition having cations with high ionic equivalent conductance to a composition having cations with low ionic equivalent conductance, thereby providing an eluent having a gradient anionic eluting strength, said eluent being maintained in a substantially isoconductive state.

3. A process as in claim 2 wherein the cationic content of the eluent changes from substantially potassium ions at the start of the process to substantially lithium ions at the end of the process.

4. A process as in claim 2 wherein the cationic content of the eluent changes from substantially cesium ions at the start of the process to substantially lithium ions at the end of the process.

5. A process as in claim 1 wherein the eluent contains borate gluconate anions.

6. A gradient ion chromatography process comprising:
   a) providing a first eluent having an anionic composition and a cationic composition;
   b) flowing said first eluent through an ion chromatography column;
   c) injecting a sample containing anions to be analyzed into the first eluent in a manner which allows the sample to flow through the ion chromatography column;
   d) increasing the eluting strength of the eluent by replacing progressively larger portions of the first eluent with a second eluent comprising a second cationic composition and a second anionic composition wherein the second anionic composition is of the same chemical identity as the first eluent but having an increased eluting strength while maintaining the eluent mixture in a substantially isoconductive state, to eliminate the need for chemical suppressors and to avoid the need for complex baseline subtraction regimens; and
   e) measuring the electrical conductivity of the eluent exiting the ion chromatography column thereby determining the presence and amount of anions in the sample.

7. A process as in claim 6 wherein the eluent has an associated, variable cationic composition which ranges between high ionic equivalent conductance to low ionic equivalent conductance, thereby allowing a variable anionic eluting strength of the eluent while maintaining the eluent in a substantially electrically isoconductive stage.

8. A process as in claim 6 wherein the eluent contains borate gluconate anions.

9. A process as in claim 6 wherein the cationic content of the eluent changes from substantially potassium ions at the start of the process to substantially lithium ions at the end of the process.

10. A process as in claim 6 wherein the cationic content of the eluent changes from substantially cesium ions at the start of the process to substantially lithium ions at the end of the process.

* * * * *